(12) United States Patent
Ho (10) Patent No.: US 9,056,177 B2
(45) Date of Patent: Jun. 16, 2015

(54) RESPIRATORY INTERFACE WITH FLEXING FACEPLATE

(75) Inventor: Peter Chi Fai Ho, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 897 days.

(21) Appl. No.: 13/132,940

(22) PCT Filed: Nov. 21, 2009

(86) PCT No.: PCT/IB2009/055247
§ 371 (c)(1),
(2), (4) Date: Jun. 6, 2011

(87) PCT Pub. No.: WO2010/067235
PCT Pub. Date: Jun. 17, 2010

(65) Prior Publication Data
US 2011/0232647 A1    Sep. 29, 2011

Related U.S. Application Data

(60) Provisional application No. 61/121,585, filed on Dec. 11, 2008.

(51) Int. Cl.
*A61M 16/06* (2006.01)
*A62B 18/02* (2006.01)
*A61M 16/10* (2006.01)

(52) U.S. Cl.
CPC ....... *A61M 16/06* (2013.01); *A61M 2202/0208* (2013.01); *A61M 16/0633* (2014.02); *A61M 16/1005* (2014.02)

(58) Field of Classification Search
USPC ............ 128/206.28, 206.21, 203.29, 205.25, 128/206.12, 206.24, 206.17, 206.15
See application file for complete search history.

(56) References Cited

U.S. PATENT DOCUMENTS

| | | | | |
|---|---|---|---|---|
| 5,505,197 | A * | 4/1996 | Scholey | 128/206.17 |
| 6,244,967 | B1 * | 6/2001 | Takabe et al. | 464/175 |
| 7,121,279 | B2 * | 10/2006 | Dennis | 128/206.21 |
| 2003/0130591 | A1 | 7/2003 | Starr et al. | |
| 2004/0035428 | A1 | 2/2004 | Olsen et al. | |
| 2007/0295331 | A1 * | 12/2007 | Crutchfield | 128/202.22 |
| 2009/0078262 | A1 * | 3/2009 | Gebrewold et al. | 128/206.12 |
| 2009/0250060 | A1 * | 10/2009 | Hacke et al. | 128/205.12 |
| 2010/0065058 | A1 * | 3/2010 | Ungar et al. | 128/206.24 |

FOREIGN PATENT DOCUMENTS

| | | |
|---|---|---|
| EP | 0634186 A2 | 1/1995 |
| FR | 2638361 A1 | 5/1990 |
| WO | 2004073778 A1 | 9/2004 |
| WO | 2006014167 A2 | 2/2006 |
| WO | 2006099603 A2 | 9/2006 |

* cited by examiner

*Primary Examiner* — Tan-Uyen (Jackie) T Ho
*Assistant Examiner* — Mark Wardas
(74) *Attorney, Agent, or Firm* — Michael W. Haas (57) ABSTRACT

Various embodiments of a respiratory interface device, such as a mask (10), that includes a first substantially rigid portion (14), a second substantially rigid portion (16) and a connecting member (18) that is structured to flexibly connect the first and second substantially rigid portions. The flexible connection provides an effective fit of the respiratory interface device against the user's face.

17 Claims, 10 Drawing Sheets

RESPIRATORY INTERFACE WITH FLEXING FACEPLATE

This patent application claims the priority benefit under 35 U.S.C. §119(e) of U.S. Provisional Application No. 61/121,585 filed on Dec. 11, 2008, the contents of which are herein incorporated by reference.

The present invention relates to respiratory interface devices for transporting a gas to and/or from an airway of a user, and in particular, to a respiratory interface device, such as a mask, that includes a flexible faceplate having first substantially rigid portion, a second substantially rigid portion, and a substantially flexible connecting member extending therebetween.

A variety of respiratory masks are known which cover the areas surrounding the nose and/or mouth of a human user and that are designed to create an effective fit against the user's face. Typically, gases can be provided at a positive pressure within the mask for consumption by the user. The uses for such masks include high altitude breathing (aviation applications), swimming, mining, fire fighting, and various medical diagnostic and therapeutic applications.

One requisite of many of these masks, particularly medical respiratory masks, is that they provide an effective fit against the user's face and that the mask contours with the user's face to limit or prevent leakage of the gas being supplied. Commonly, in conventional mask configurations, an effective mask-to-face fit has been attained in many instances only with considerable discomfort for the user. This problem is most crucial in those applications, especially medical applications, which require the user to wear the mask continuously for hours or perhaps even days, and during sleep or falling to sleep. In such situations, the user often will not tolerate the mask for long durations and therefore optimum therapeutic or diagnostic objectives will not be achieved, or will be achieved with great difficulty and considerable user discomfort.

Several types of respiratory masks for the types of applications mentioned above are known. Perhaps the most common type of mask incorporates a single-piece faceplate or a two-piece faceplate, having an upper portion (e.g., to cover the nasal portion of a human user's face) and lower portion (e.g., to cover the mouth portion of a human user's face) that are attached. Both of these portions are made from a substantially rigid material and unitary piece of material.

The respiratory masks that are known can also have a sealing surface or cushion around the periphery of the mask to seal against the user's face. The cushion is typically attached to the faceplate. Such masks have performed well when the fit is good between the contours of the seal surface and the corresponding contours of the user's face. This may occur, for example, if the mask provides a good fit against the user's face and the mask contours with the user's face. If the fit is not good, there will be gaps in the mask-to-face interface resulting in gas leaking from the mask at the gaps. Considerable force will be required to compress the mask member to close the gaps and attain a satisfactory seal in those areas where the gaps occur. Typically, this required force will be provided by straps that are connected to the mask to securely fit the mask to the face of the user. Such force is undesirable because it produces high pressure points elsewhere on the face of the user where the mask contour is forcibly deformed against the face to conform to the user's facial contours. This will produce considerable user discomfort and possible skin irritation and breakdown anywhere the applied force exceeds the local perfusion pressure, which is the pressure that is sufficient to cut off surface blood flow.

In one embodiment, the invention provides a respiratory interface device including a first substantially rigid portion, a second substantially rigid portion, and a flexible connecting member. The connecting member extends between the first portion and the second portion to at least partially connect the first portion to the second portion and to permit the first portion and the second portion to flex relative to one another. The first substantially rigid portion can be structured to accommodate a nasal region of a user and the second substantially rigid portion can be structured to accommodate an oral region of a user. Further, the connecting member can have a concave shape relative to a front of the respiratory interface device. Alternatively, the connecting member can have a convex shape relative to a front of the respiratory interface device. The connecting member can be structured to flex in a hinge-like manner. The connecting member can be structured to have a variable wall thickness. The wall thickness can be in the range of from about 0.5 to about 3 mm. The connecting member can be constructed of a material having an elongation in the range of from about 600% to about 800%. The connecting member can be constructed of a material selected from the group consisting of thermoplastics, thermoelastomers, and combinations thereof. The connecting member can include a hinge mechanism. The hinge mechanism can include a living hinge.

In one embodiment of the invention, the respiratory interface device can further include a third substantially rigid portion, a fourth substantially rigid portion, a second flexible connecting member and a third flexible connecting member. The second flexible connecting member can extend between the first substantially rigid portion and the third substantially rigid portion and can permit the first substantially rigid portion and the third substantially rigid portion to flex relative to one another. The third flexible connecting member can extend between the second substantially rigid portion and the fourth substantially rigid portion and can permit the second substantially rigid portion and the fourth substantially rigid portion to flex relative to one another. The flexible connecting member also can extend between the third substantially rigid portion and the fourth substantially rigid portion and can permit the third substantially rigid portion and the fourth substantially rigid portion to flex relative to one another.

Further, an additional support member can be at least partially connected to the first substantially rigid portion of the respiratory interface device for engaging a portion of the face of the user. The first substantially rigid portion can have a first opening and the second substantially rigid portion can have a second opening. The first opening can include an exhaust port and the second opening can be coupled to a coupling device. Alternatively, the first opening can be removably coupled to an exhaust valve and the second opening can be removably coupled to a coupling device. In another alternative, the first opening can be removably coupled to a cap and the second opening can be removably coupled to a coupling device.

In another aspect, the second substantially rigid portion can be removably coupled to the respiratory interface device. Further, the first and second substantially rigid portions can be structured to accommodate an oral region of the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the term "interface device" refers to any suitable mechanism for transporting gas to and/or from the airway of a user and expressly includes, but is not limited to, non-invasive interface devices such as masks (e.g., without limitation, masks including support elements such as forehead supports and cheek pads and full face masks such as the Total™ face mask sold by the assignee hereof). As employed herein, the statement that two or more parts or components are "coupled" or "connected" together shall mean that the parts are joined or operate together either directly or through one or more intermediate parts or components. As employed herein, the term "number" shall mean one or an integer greater than one (i.e., a plurality).

Figure 1:
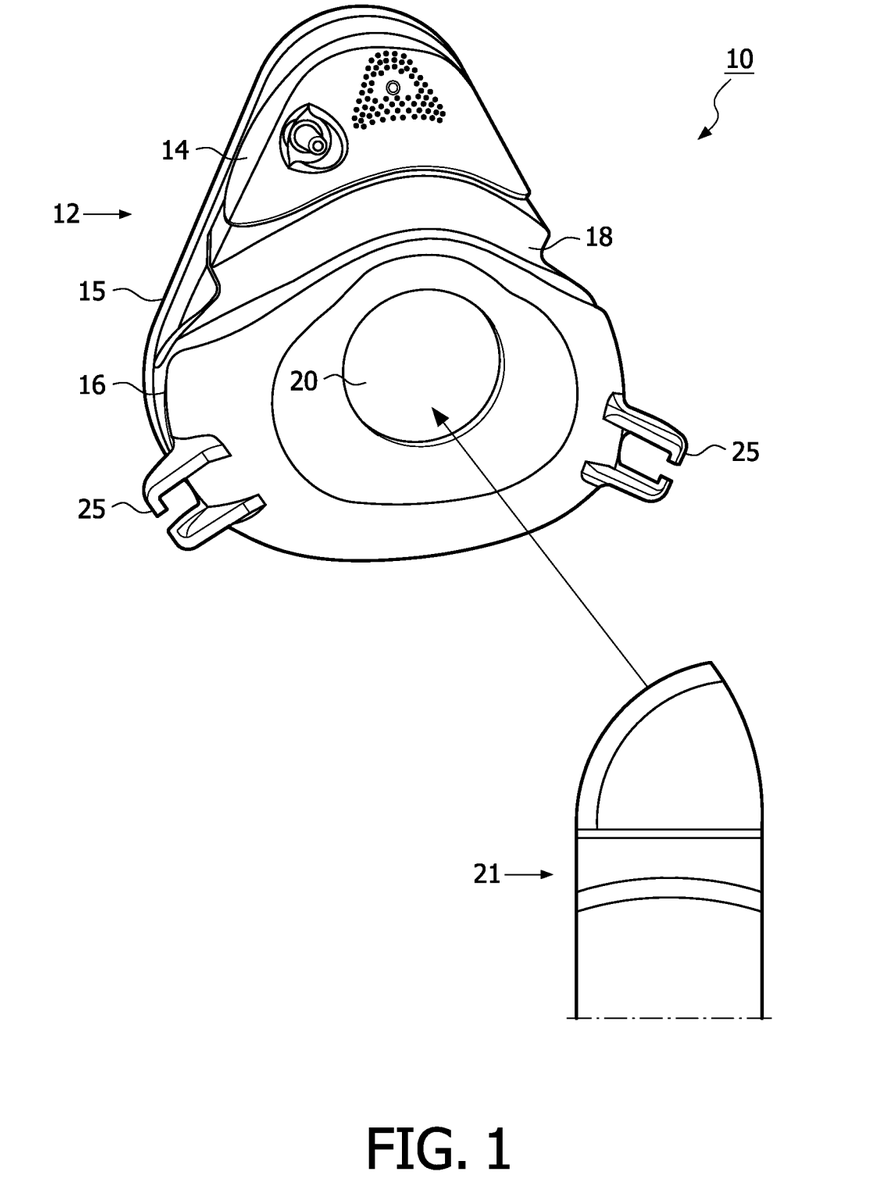
FIG. 1 is a front isometric view of a respiratory mask according to an embodiment of the invention.

FIG. 1 is a front isometric view of a respiratory mask 10 according to an embodiment of the invention. Mask 10 coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV®) device, proportional positive airway pressure (PPAP) device, C-Flex™ device, Bi-Flex® device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

Respiratory mask 10 includes body 12 having upper portion 14 and lower portion 16. Body 12 further includes substantially flexible connecting member 18 that extends between upper and lower portions 14 and 16, respectively. Connecting member 18 is structured to at least partially connect upper portion 14 to lower portion 16. Specifically, a first side of connecting member 18 is coupled to upper portion 14 and a second, opposite side, is coupled to lower portion 16.

Upper and lower portions 14,16 are typically, although not necessarily, generally rigid, whereas connecting member 18 is a flexible, resilient member. In an exemplary embodiment of the present invention, connecting member 18 made of, for example, a thermoplastic or thermoelastic material, including but not limited to an elastomer such as plastic, rubber, silicone, vinyl, foam, or any combination thereof.

It is contemplated in the present invention that connecting member 18 can be formed in various shapes and geometries. In one embodiment, connecting member 18 provides a groove between upper and lower portions 14,16. The groove (as shown in FIG. 1) can be structured to form a concave shape (e.g., an inward barrel shape). Alternatively, the groove can form a convex shape (e.g., an outward barrel shape).

Connecting member 18 is structured to be flexible such that it can move in a hinge-like manner (as shown in FIG. 1). Such hinge-like movement allows upper portion 14 to flex or move independently or separately from and relative to lower portion 16. Thus, mask 10 can provide improved contouring to the user's face, and therefore result in an effective fit. The particular connecting member 18 shown in FIG. 1 is not meant to be limiting and it should be understood that the present invention contemplates a variety of different configurations for the flexible connecting member which are described in more detail elsewhere herein. Thus, various flexible connecting members may be substituted for connecting member 18.

Suitable materials for constructing connecting member 18 can be selected from a wide variety of flexible, elastic materials known in the art or hereafter developed. Suitable materials can include but are not limited to those previously described herein. In an embodiment, connecting member 18 can be constructed of a material having a Shore A hardness of from about 20 to about 40, or a material having an elongation of between about 600% and about 800%. In one particular embodiment, the material from which connecting member 18 is made is silicone rubber.

Further, connecting member 18 can have a generally uniform wall thickness, or, alternatively, the thickness can be variable. For example, the wall thickness of the central groove portion of connecting member 18 may be less than the wall thickness outside the central groove portion. The wall thickness is typically in the range of from about 0.5 to about 3 mm.

In one embodiment, connecting member 18 is constructed of a material having a Shore A hardness of about 40, an elongation of about 600% and a wall thickness of from about 0.5 to about 1.5 mm. In another embodiment, connecting member 18 is constructed of a material having a Shore A hardness of about 20, an elongation of about 800% and wall thickness of from about 1 to about 3 mm.

Connecting member 18 can be structured to be integrally connected to upper and lower portions 14,16 (as shown in FIG. 1). For example, upper portion 14, lower portion 16 and connecting member 18 can together form a single-piece body comprising body 12. In another embodiment (not shown), connecting member 18 can be structured to be detachably connected to one or both of upper and lower portions 14,16 such that upper portion 14, lower portion 16, and connecting member 18 can form a two-piece or three-piece body, as described in more detail elsewhere herein.

In the embodiment as shown in FIG. 1, lower portion 16 also defines lower opening 20. Lower opening 20 can function as a gas inlet. In the embodiment shown in FIG. 1, the gas inlet (lower opening 20) can be coupled to coupling device 21, such as a swivel conduit, for carrying gas such as air between mask 10 and an external gas source (not shown), such as a blower, or any other suitable device. It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure (BiPAP) therapy, as noted above.

The particular coupling device 21 shown in FIG. 1 is not meant to be limiting and it should be understood that the present invention contemplates a variety of different coupling devices that could be attached, either permanently or selectively, to lower opening 20 to carry gas to or from mask 10. Thus, a variety of coupling devices (e.g., with or without swivels on one or both ends, and with or without an exhalation system formed integral to the device) may be substituted for coupling device 21. As also seen in FIG. 1, upper portion 14 includes a venting mechanism, such as exhaust port 22, for exhausting gas expired by the user to the atmosphere. It is to be understood that exhaust port 22 is optional or can be provided at other locations on the mask, patient circuit, or both.

In the illustrated exemplary embodiment, exhaust port 22 includes a plurality of small openings that allow the exhaust gas expired by the user to exit mask 10 to the atmosphere. The particular configuration for exhaust port 22 shown in FIG. 1 is not meant to be limiting and it should be understood that the present invention contemplates a variety of different venting mechanisms that could be employed to exhaust the gas expired by the user to the atmosphere. Thus, a variety of venting mechanisms may be substituted for exhaust port 22. In addition, other exhaust vent devices can be used in place of or in addition to exhaust port 22.

Further, as seen in FIG. 1, upper portion 14 includes pressure/oxygen port 23 which allows for obtaining a pressure reading or providing an additional supply of oxygen. Again, the specific configuration, number, and location for pressure/oxygen port 23 is not meant to be limited. Instead, the present invention contemplates that pressure/oxygen port 23 can have a variety of configurations, include multiple ports, and can be provide at various locations on the mask or omitted entirely.

Mask 10 in FIG. 1 also includes fastening devices, such as tabs 25 or the like, that connect to suitable adjustable retention straps (not shown) for retaining the mask 10 with respect to the user's face. Although two such tabs 25 are illustrated in FIG. 1 at selected corners of mask 10, it is to be understood that other configurations, arrangements, numbers (including none) and locations of fastening devices are contemplated by the present invention, as described in more detail elsewhere herein.

Figure 2:
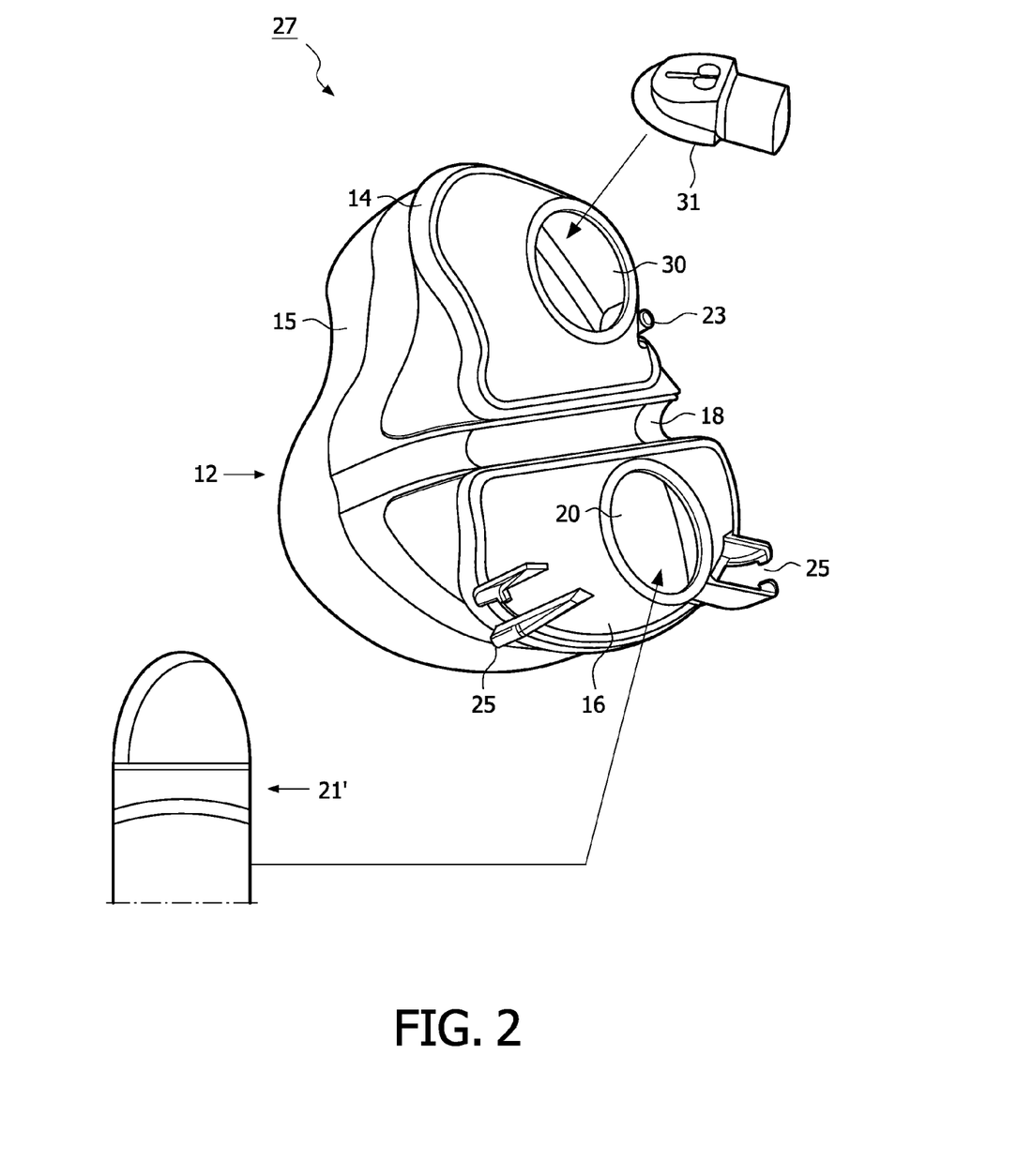
FIGS. 2, 3, 4, and 5 are front isometric views of a respiratory mask according to alternate embodiments of the invention.

FIG. 2 is a front isometric view of respiratory mask 27 according to an alternative embodiment of the invention. As seen in FIG. 2, mask 27 includes a number of the same components included as part of mask 10 in FIG. 1, including upper portion 14, lower portion 16 and connecting member 18. In addition, as shown in FIG. 2, upper portion 14 thereof defines upper opening 30. Thus, in the embodiment shown in FIG. 2, mask 27 includes two openings, upper opening 30 and lower opening 20.

Preferably, one of upper opening 30 and lower opening 20 functions as a gas inlet while the other of upper opening 30 and lower opening 20 functions as a gas outlet. For instance, as shown in FIG. 2, coupling device 21, such as any type of conduit as described in more detail elsewhere herein (and with or without swivels), is removably attached to lower opening 20 for carrying a gas, such as air, between mask 27 and an external gas source (not shown), such as a blower or any other suitable device as described in more detail elsewhere herein. Upper opening 30 may then function as an outlet for purging carbon dioxide from mask 27.

Also, as shown in FIG. 2, an exhalation venting mechanism, such as without limitation exhaust valve 31, for exhausting gas expired by the user to the atmosphere, is removably coupled to the outlet (upper opening 30). The particular exhaust valve 31 as shown in FIG. 2 is not meant to be limiting and it should be understood that the present invention contemplates a variety of different venting mechanisms that could be employed to exhaust the gas expired by the user to the atmosphere, as described in more detail elsewhere herein. Thus, a variety of venting mechanisms may be substituted for exhaust valve 31.

Alternatively, the present invention also contemplates that coupling device 21 may be removably attached to upper opening 30, in which case, lower opening 20 will function as the outlet for purging exhaust gas.

Figure 3:
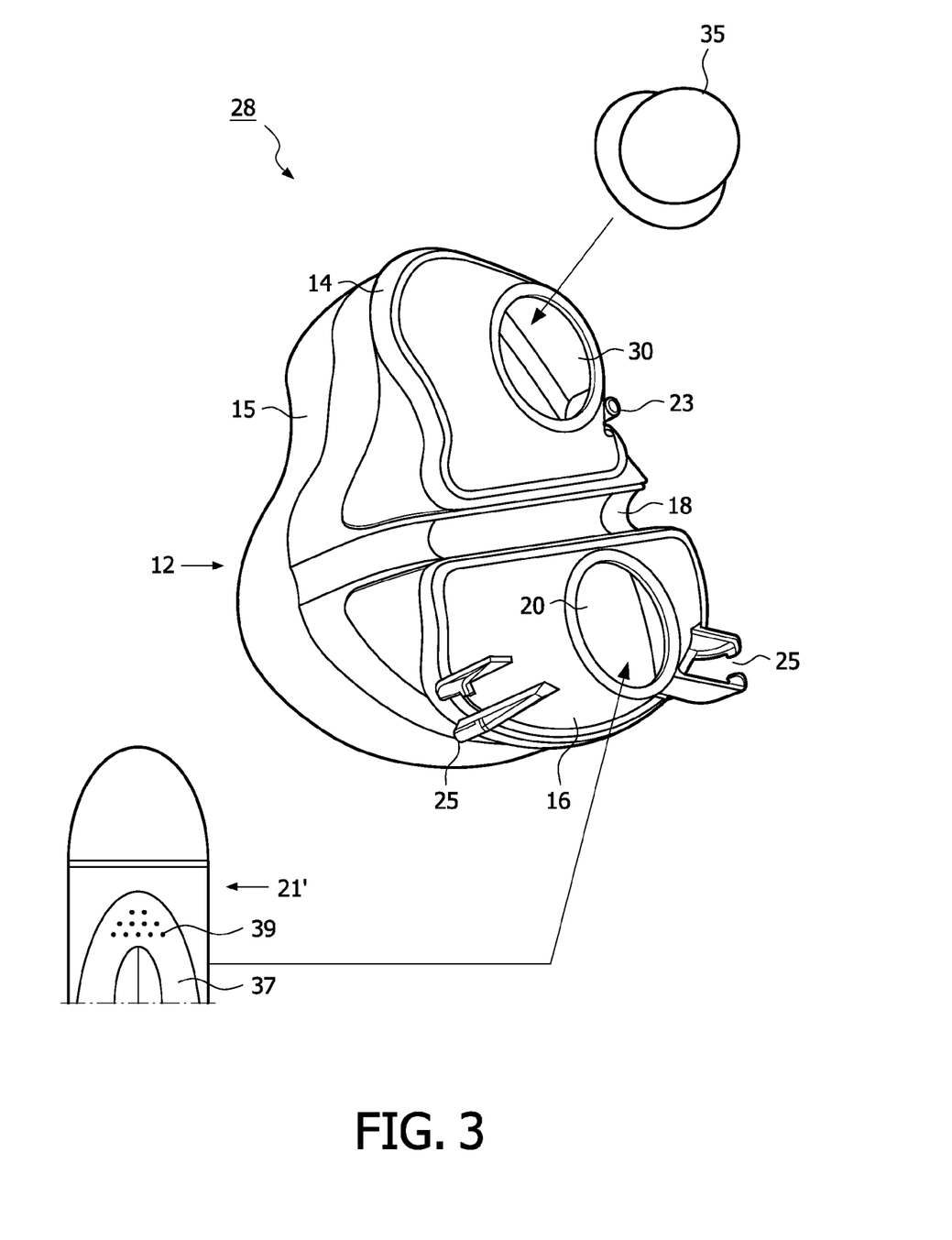

FIG. 3 is a front isometric view of respiratory mask 28 according to an alternative embodiment of the invention. As shown in FIG. 3, mask 28 includes a number of the same components included as part of mask 10 in FIG. 1 and mask 27 in FIG. 2. In addition, as shown in FIG. 3, mask 28 includes a cap 35 removably coupled to upper opening 30 in upper portion 14 to cover upper opening 30. In this embodiment, upper opening 30 is not being used to function as either a gas inlet or an exhalation outlet. Instead, lower opening 20 functions as both the gas inlet and exhalation outlet.

As also seen in FIG. 3, a coupling device 21', such as any conduit capable of carrying a gas such as air between mask 28 and an external gas source (not shown), such as a blower or any other suitable device, is removably coupled to the gas inlet. As also seen in FIG. 3, coupling device 21' in this embodiment includes a venting mechanism, such as exhaust port 37 for exhausting gas expired by the user to the atmosphere. Exhaust port 37 includes a plurality of small openings 39 as shown in FIG. 3, that allow the exhaust gas expired by the user to exit mask 28 to the atmosphere. The particular coupling device 21', external gas source and exhaust port 37 as shown in FIG. 3, are each not meant to be limiting and it should be understood that other types of coupling devices, external gas sources and venting mechanisms, as described in more detail elsewhere herein, may be substituted for the each of coupling device 21', external gas source and exhaust port 37 shown in FIG. 3.

Alternatively, the present invention contemplates that coupling device 21', shown in FIG. 3, may be removably attached to upper opening 30, in which case lower opening 20 would be capped with cap 35.

Masks 10, 27, and 28 as shown in FIGS. 1, 2, and 3 are oral/nasal masks that accommodate both the oral and nasal regions of the user's face. Upper portion 14 in each of the embodiments can accommodate the nasal region, and lower portion 16 can accommodate the oral region. As is conventional, mask body 12 and/or upper and lower portions 14, 16 also preferably includes fastening devices, such as tabs 25 or the like, that connect to suitable adjustable retention straps (not shown) for retaining the mask with respect to the user's face. Although two such tabs 25 are illustrated in FIGS. 1, 2, and 3, and are generally arrayed at selected corners of mask 10, 27 or 28, as the case may be, the particular tabs 25 shown in FIGS. 1, 2 and 3 are not meant to be limiting and it should be understood that other types of fastening devices that will aid in retaining the mask with respect to the user's face may be substituted for tabs 25. Further, it should be understood that various other arrangements, numbers (including none)

and locations of fastening devices can be provided without deviating from the principles of the present invention.

As shown in FIGS. 1, 2, and 3, masks 10, 27, and 28 includes patient contacting cushion 15. In an exemplary embodiment, cushion 15 is integrally connected to upper portion 14, lower portion 16, and connecting member 18. Cushion 15 is structured to extend toward the user's face and generally defines the depth of mask 10, 27 or 28. In an exemplary embodiment, a portion of cushion 15 defines all or at least a portion of connecting member 18.

Cushion 15 can be constructed of a wide variety of materials known in the art and can include but is not limited to those materials previously described as suitable materials for upper and lower portions 14,16 and connecting member 18. The particular cushion 15 shown in FIGS. 1, 2, and 3 is not meant to be limiting and it should be understood that other types of cushion supports or sealing systems that extend between the frame member (e.g., faceplate 12 shown in FIGS. 1, 2 and 3) and the user's face, may be substituted for cushion 15. For example, and without limitation, various cushion configurations can include a double flap cushion, a gel cushion, a gel cushion with a flap, an air-filled cushion, a cushion with a pleat, multiple cushions (e.g., one inside of the other). Further, it is to be understood that the cushion (e.g., cushion 15 in FIGS. 1, 2 and 3) can be detachable and removable from the frame member (e.g., faceplate 12 in FIGS. 1, 2, and 3).

Figure 4:
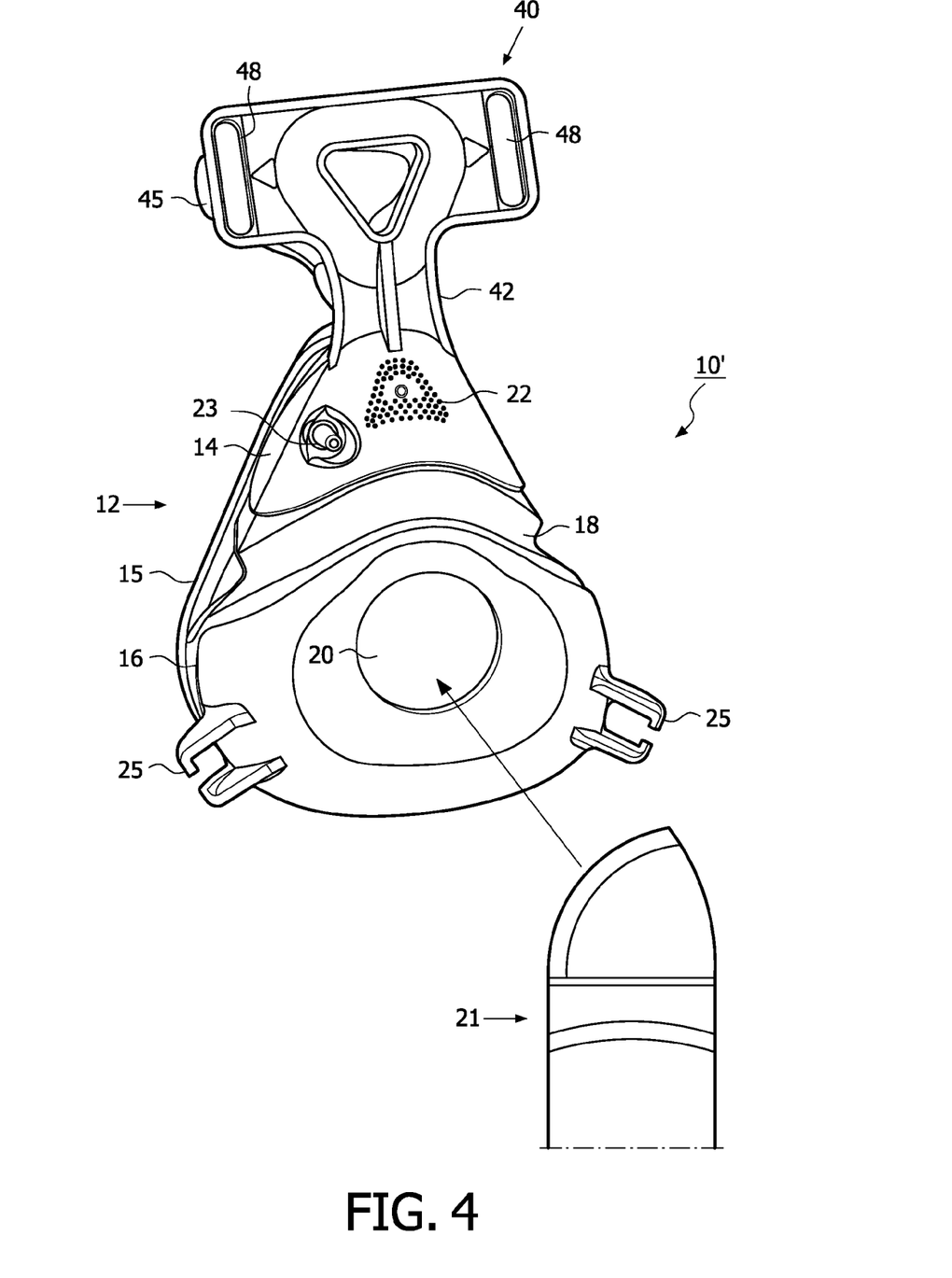

FIG. 4 is a front isometric view of respiratory mask 10' according to yet another embodiment of the invention. As seen in FIG. 4, mask 10' includes a number of the same components included as part of mask 10 in FIG. 1. In addition, as shown in FIG. 4, mask 10' further includes forehead support 40 connected to and extending from upper portion 14 of mask body 12 through support arm 42. Forehead support 40 includes engagement surface 45 structured to engage the forehead of the user. Forehead support 40 includes two openings or slits 48 structured to have two top straps (not shown) extending therefrom in order to assist in holding the mask in place (not shown).

Figure 5:
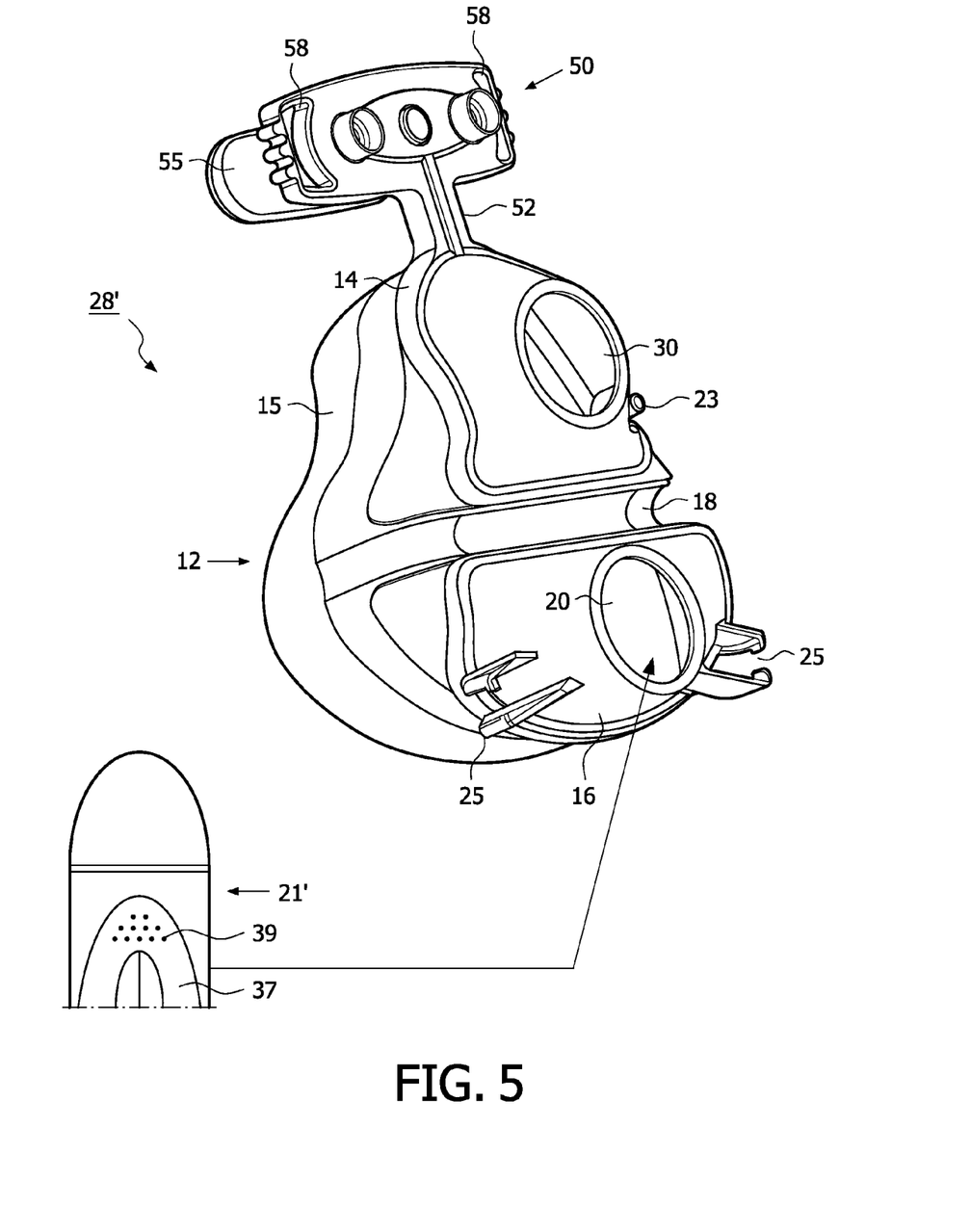

FIG. 5 is a front isometric view of respiratory mask 28' according to yet another embodiment of the invention. As seen in FIG. 5, mask 28' includes a number of the same components included as part of mask 28 in FIG. 3. In addition, as shown in FIG. 5, mask 28' further includes forehead support 50 connected to and extending from upper portion 14 of mask body 12 through support arm 52. Forehead support 50 includes engagement surface 55 structured to engage the forehead of the user. Forehead support 50 includes two openings or slits 58 structured to have two top straps (not shown) extending therefrom in order to assist in holding the mask in place (not shown).

Forehead supports 40 and 50 shown in FIGS. 4 and 5, respectively, are shown for illustrative purposes as one particular type of facial support and are not meant to be limiting. It should be understood that any other types of facial supports (or none), such as, without limitation, cheek pads, can be used in place of or in addition to forehead support 40,50. Further, the facial support (e.g., forehead support 40, 50) can be removable, adjustable, or fixed.

FIGS. 6A, 6B, 6C, 6D, and 6E are front isometric views of masks 13a, 13b, 13c, 13d, and 13e having alternative connecting members 18a, 18b, 18c, 18d, and 18e according to particular non-limiting embodiments of the present invention. In FIGS. 6A through 6E, flexible connecting member 18a-18e extends between upper portion 14a-14e and lower portion 16a-16e. Upper portion 14a-14e and lower portion 16a-16e may be, but are not necessarily, constructed of a substantially rigid material. As shown in FIGS. 6A through 6E, flexible connecting member 18a-18e may be formed in a variety of shapes and configurations.

Figure 6A:
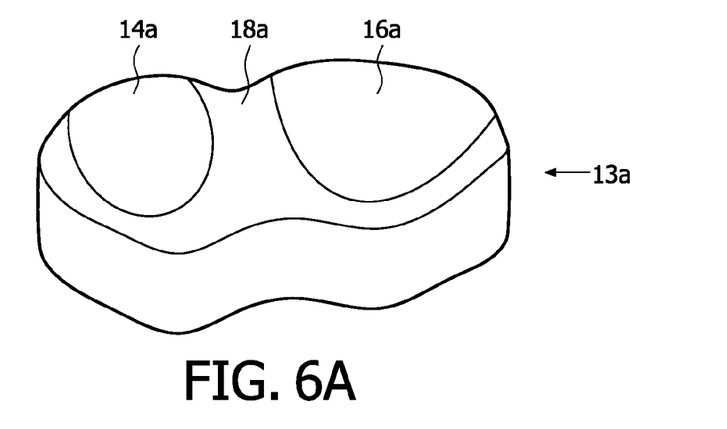
FIGS. 6A, 6B, 6C, 6D, and 6E are front isometric views of masks showing a connecting member according to alternate embodiments of the invention.
Figure 6B:
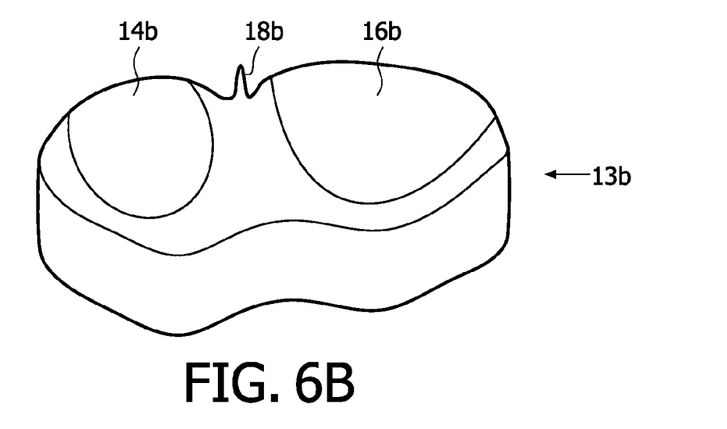
Figure 6C:
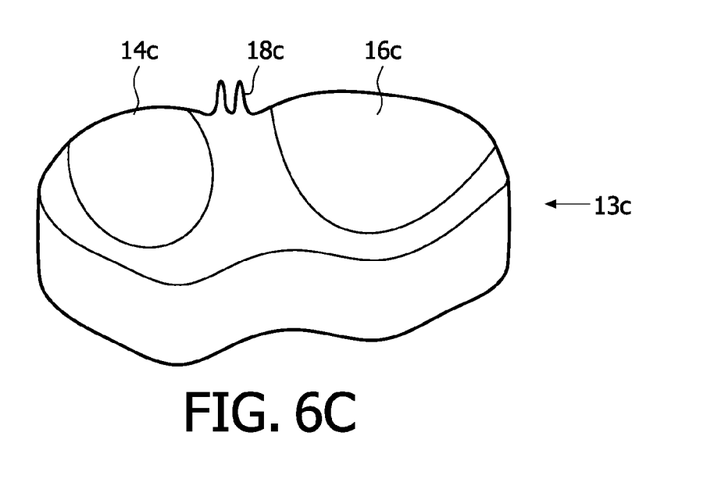
Figure 6D:
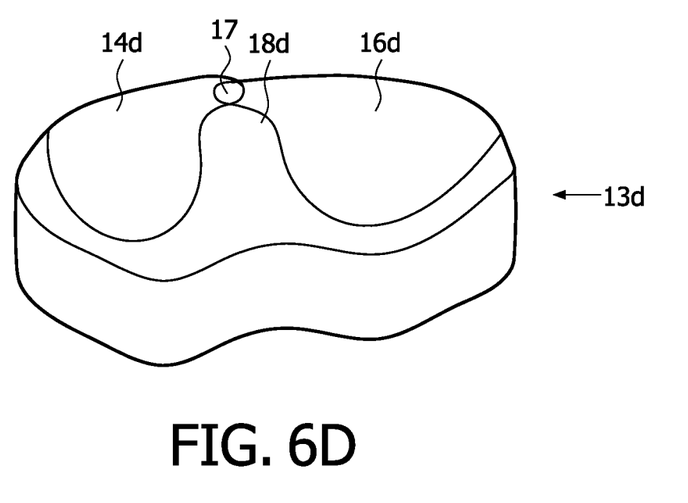
Figure 6E:
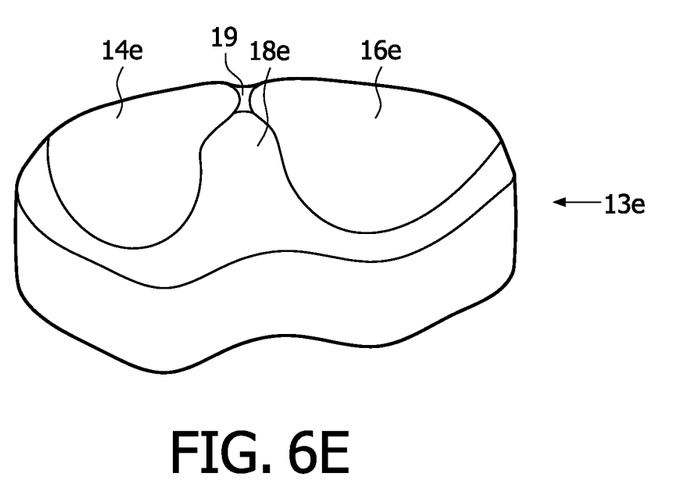

In FIG. 6A, flexible connecting member 18a extends completely between upper portion 14a and lower portion 16a. Flexible connecting member 18a is structured as a flap having a variable thickness such that upper portion 14a and lower portion 16a can flex relative to one another. In FIG. 6B, flexible connecting member 18b extends completely between upper portion 14b and lower portion 16b. Flexible connecting member 18b is structured to form a pleat therein. In FIG. 6C, flexible connecting member 18c extends completely between upper portion 14c and lower portion 16c. Flexible connecting member 18c is structured to form two pleats therein. In FIG. 6D, flexible connecting member 18d extends partially between upper portion 14d and lower portion 16d. Upper portion 14d and lower portion 16d are connected by mechanical hinge structure 17 which allows upper portion 14d to flex relative to lower portion 16d. In FIG. 6E, flexible connecting member extends partially between upper portion 14e and lower portion 16e. Upper portion 14e and lower portion 16e are connected therebetween by living hinge mechanism 19.

The term "living hinge" refers to a flexible hinge that is typically made from plastic that joins two substantially rigid parts together, allowing them to bend along a line of the hinge. The "line of the hinge" is typically a thinned section of the plastic that is capable of bending. Various types of plastic may be used to make living hinge 19, such as, without limitation, polyethylene and polypropylene due to their fatigue resistant properties. Living hinge 19 may be manufactured in an injection molding operation and can be molded in the same molding process used to create the two pieces (14e and 16e) joined by living hinge 19.

Figure 7:
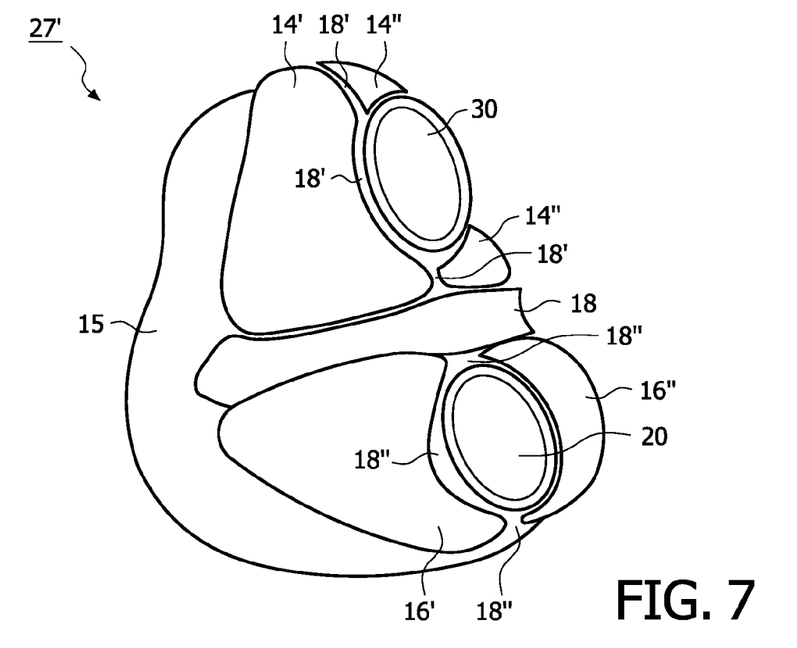
FIG. 7 is a front isometric view of a respiratory mask according to a further alternate embodiment of the invention.

FIG. 7 is a front isometric view of respiratory mask 27' according to an alternative embodiment of the invention. As seen in FIG. 7, mask 27' includes a number of the same components included as part of mask 27 in FIG. 2, including upper opening 30, lower opening 20, and cushion 15. In addition, mask 27' includes first upper portion 14' and second upper portion 14". Substantially flexible connecting member 18' extends partially between first upper portion 14' and second upper portion 14". Connecting member 18' is structured to at least partially connect first upper portion 14' to second upper portion 14". Connecting member 18' also extends along the outer peripheral edge of upper opening 30 such that connecting member 18' is structured to at least partially connect first upper portion 14' to a portion of the outer peripheral edge of upper opening 30, and to at least partially connect second upper portion 14" to an opposite portion of the outer peripheral edge of upper opening 30.

Also, as shown in FIG. 7, mask 27' includes first lower portion 16' and second lower portion 16". Substantially flexible connecting member 18" extends partially between first lower portion 16' and second lower portion 16". Connecting member 18" is structured to at least partially connect first lower portion 16' to second lower portion 16". Connecting member 18" also extends along the outer peripheral edge of lower opening 20 such that connecting member 18" is structured to at least partially connect first lower portion 16' to a portion of the outer peripheral edge of lower opening 20, and to at least partially connect second lower portion 16" to an opposite portion of the outer peripheral edge of lower opening 20. It is contemplated that the connecting member 18' allows the first and second upper portions 14',14" to flex relative to one another (e.g., from side-to-side), and the connecting member 18" allows the first and second lower portions 16',16" to flex relative to one another (e.g., from side-to-side).

Figure 8:
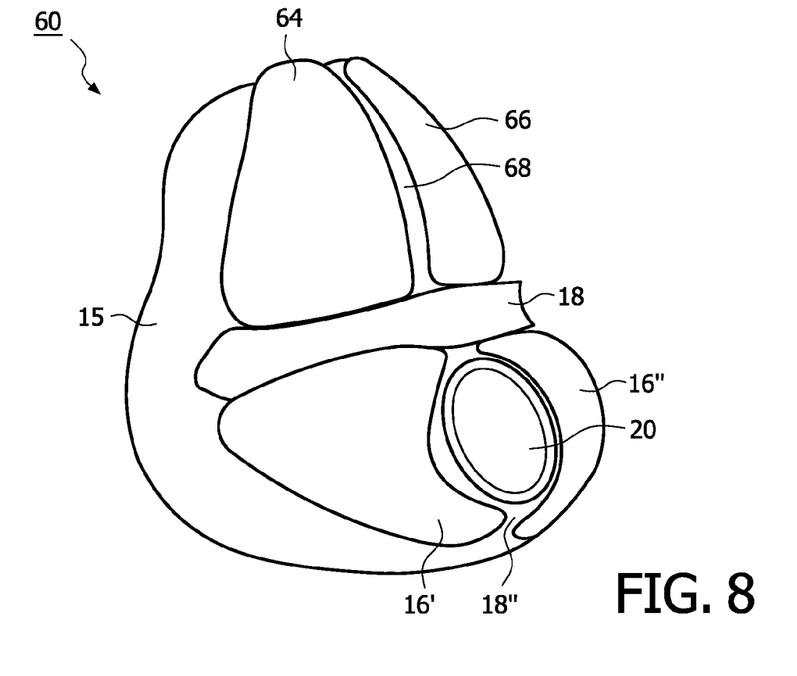
FIG. 8 is a front isometric view of a respiratory mask according to still a further alternate embodiment of the invention.

FIG. 8 is a front isometric view of respiratory mask 60 according to an alternative embodiment of the invention. As seen in FIG. 8, mask 60 includes a number of the same components included as part of mask 27' in FIG. 7, including first lower portion 16', second lower portion 16", connecting members 18,18", lower opening 20, and cushion 15. Mask 60 includes first upper portion 64 and second upper portion 66. Substantially flexible connecting member 68 extends completely between first upper portion 64 and second upper portion 66. Connecting member 68 is structured to connect first upper portion 64 to second upper portion 66. Specifically, a first side of connecting member 68 is coupled to first upper portion 64 and a second, opposite side, of connecting member 68 is coupled to second upper portion 66.

Also, as shown in FIG. 8, mask 60 includes first lower portion 16' and second lower portion 16". Substantially flexible connecting member 18" extends partially between first lower portion 16' and the second lower portion 16". Connecting member 18" is structured to at least partially connect first lower portion 16' to second lower portion 16". Connecting member 18" also extends along the outer peripheral edge of lower opening 20 such that connecting member 18" is structured to at least partially connect first lower portion 16' to a portion of the outer peripheral edge of lower opening 20, and to at least partially connect second lower portion 16" to a portion of the outer peripheral edge of lower opening 20. It is contemplated that connecting member 68 allows first and second upper portions 64,66 to flex relative to one another (e.g, from side-to-side), and connecting member 18" allows first and second lower portions 16',16" to flex relative to one another (e.g., from side-to-side).

Figure 9:
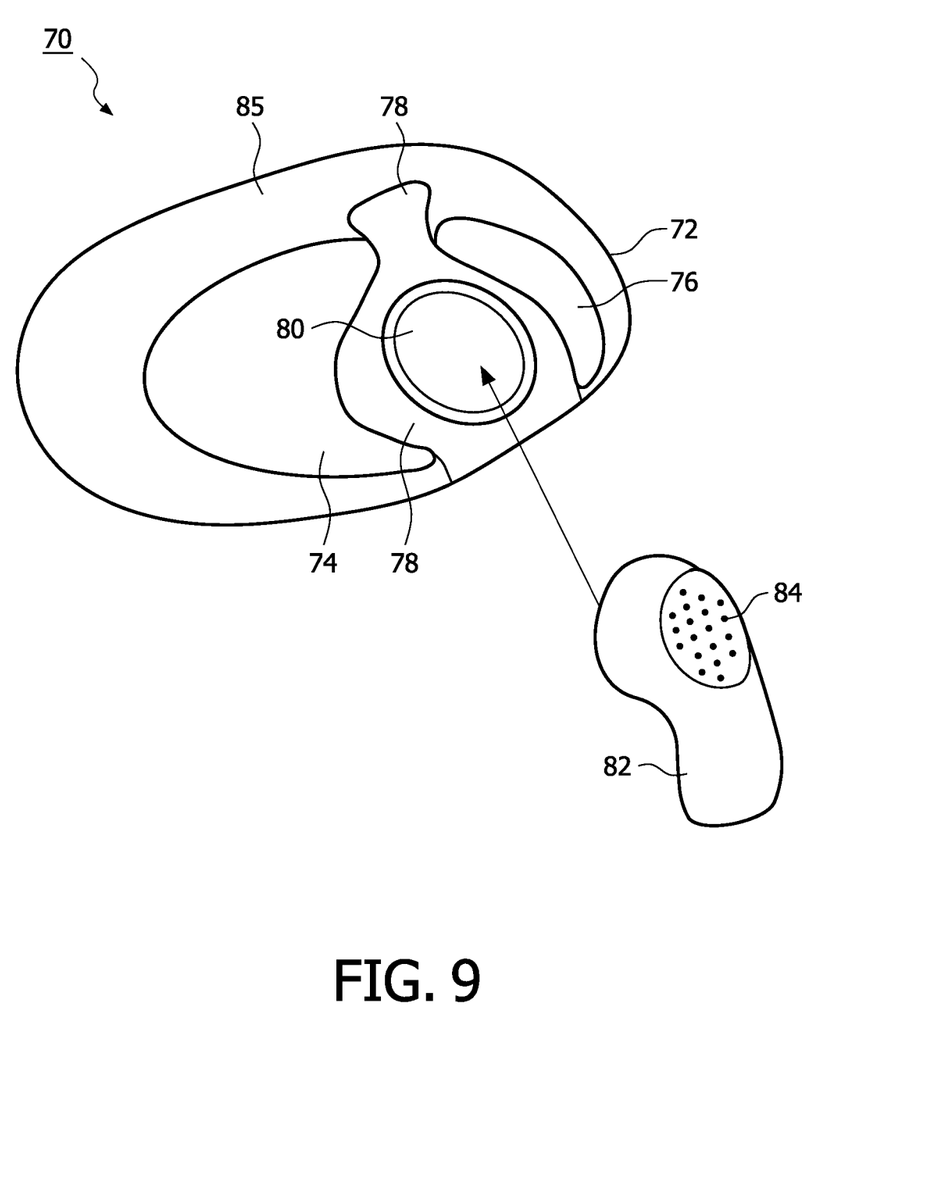
FIG. 9 is a front isometric view of a respiratory mask according to yet another alternate embodiment of the invention.

FIG. 9 is a front isometric view of a respiratory mask 70 according to an alternative embodiment of the invention. As seen in FIG. 9, mask 70 is structured to accommodate the oral region only of the user's face. Respiratory mask 70 includes body 72 having first side portion 74 and second side portion 76. Body 72 further includes substantially flexible connecting member 78 that extends at least partially between first and second side portions 74,76. Connecting member 78 is structured to at least partially connect first side portion 74 to second side portion 76. First and second side portions 74, 76 are typically, although not necessarily, generally rigid, whereas connecting member 78 is a flexible (preferably solid), resilient member made of, for example, the materials described elsewhere herein for substantially flexible connecting member 18.

Also, as shown in FIG. 9, connecting member 78 extends along the outer peripheral edge of opening 80 such that connecting member 78 is structured to at least partially connect first side portion 74 to a portion of the outer peripheral edge of opening 80, and to at least partially connect second side portion 76 to an opposite portion of the outer peripheral edge of opening 80. It is contemplated that connecting member 78 allows the first and second side portions 74,76 to flex relative to one another (e.g., from side-to-side)

Also, as shown in FIG. 9, opening 80 can function as a gas inlet to transport gas such as air from an external gas source (not shown) to a user and/or a venting mechanism for exhausting gas expired by the user to the atmosphere. Opening 80 can be coupled to coupling device 82. Coupling device 82 is an elbow having venting holes 84 integrally formed therein. The particular coupling device 82 and venting mechanism (i.e., venting holes 84) shown in FIG. 9 are not meant to be limiting and it should be understood that the present invention contemplates a variety of different coupling devices and venting mechanisms that could be employed, including, without limitation, those described in more detail elsewhere herein.

As shown in FIG. 9, the mask 70 also includes a cushion 85. Cushion 85 is preferably integrally connected to the first side portion 74, the second side portion 76 and the connecting member 78. Cushion 85 can be structured in various configurations and constructed of a variety of materials, such as, without limitation those configurations and materials described in more detail elsewhere herein.

Figure 10:
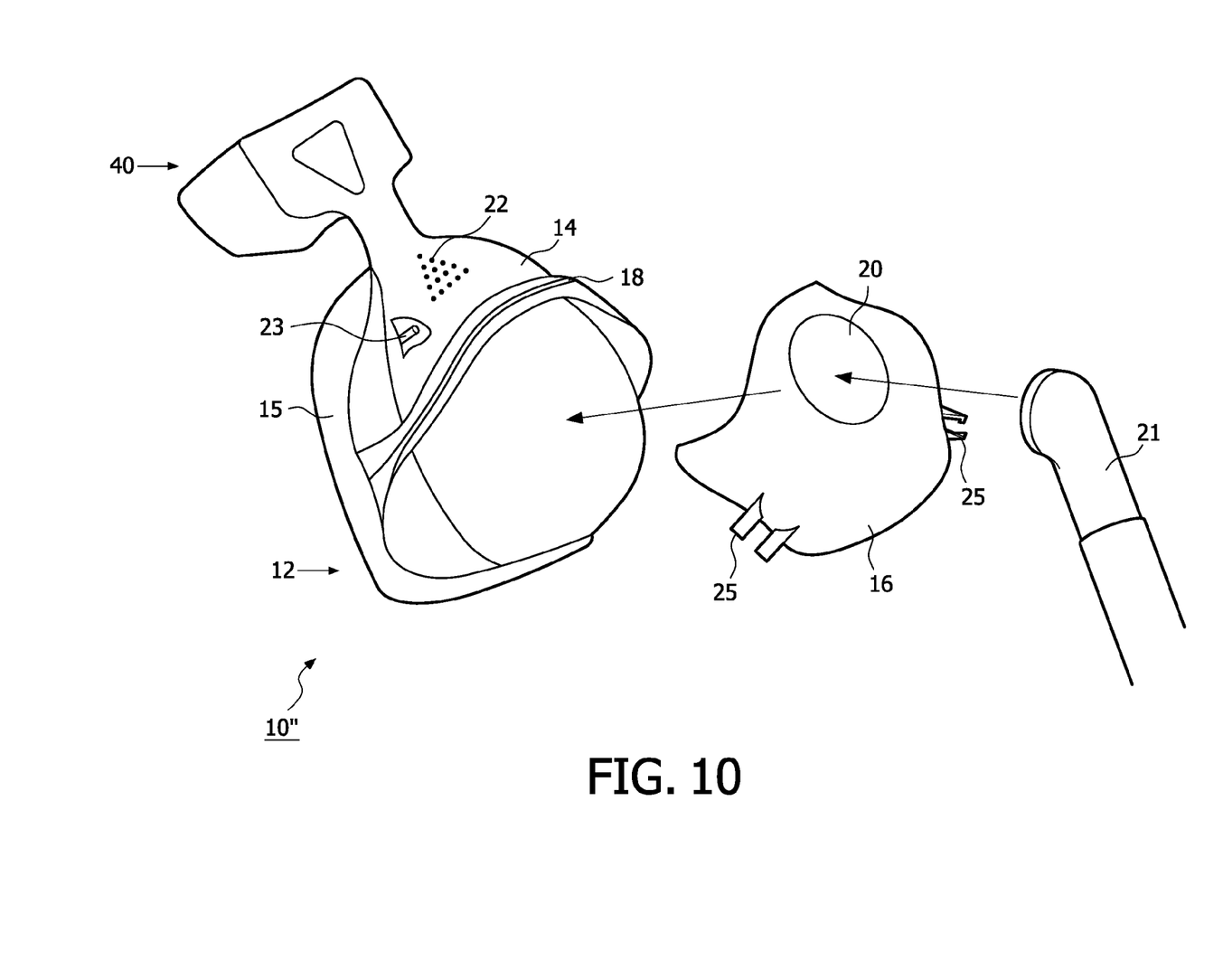
FIG. 10 is a front isometric view of a respiratory mask according to still a further alternate embodiment of the invention.

FIG. 10 is a front isometric view of respiratory mask 10" according to yet another embodiment of the invention. As seen in FIG. 10, mask 10" includes a number of the same components included as part of mask 10' in FIG. 4, including body 12, upper portion 14, lower portion 16, connecting member 18, lower opening 20, cushion 15, exhaust port 22, pressure/oxygen port 23, tabs 25 and coupling device 21. As shown in FIG. 10, mask 10" includes coupling device 21 that is removable from lower portion 16, and lower portion 16 that is removable from body 12.

The mask according to the various embodiments of the present invention contours to the face of the user to provide an effective fit that is relatively comfortable for the user. In addition, various other mechanisms can be employed to assist in providing a secure fit of the mask to the user's face. For instance, the contact surface of the mask can include an adhesive layer thereon. The adhesive layer provides a bonding seal between the mask and the user's skin. The adhesive layer is made of a bonding agent that can be provided on and bonded to the contact surface of the mask. The adhesive layer should have a level of stickiness that will cause it to temporarily bond to the skin of the user of the mask, preferably without leaving a significant amount of residue when removed. The adhesive layer will thus provide a bonding seal between the mask and the user's skin so as to reduce and/or eliminate leaks.

The adhesive layer can be used instead of, or in addition to, straps. As described above, straps are connected to the mask at one or more locations such as at the lower portion of the mask on opposite sides thereof and on the upper portion of the mask on opposite sides. For masks with a forehead support, straps can be attached to opposite sides of the forehead support.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory interface device, comprising:
a first substantially rigid element;
a second substantially rigid element that is discrete from the first substantially rigid element;
a third substantially rigid element;
a fourth substantially rigid element that is discrete from the third substantially rigid element;
a first flexible connecting member of a substantially impervious material that is substantially more flexible than the first and second substantially rigid elements extending between the first substantially rigid element and the second substantially rigid element to at least partially connect the first substantially rigid element to the second substantially rigid element, and to enable the first substantially rigid element and the second substantially rigid element to flex relative to one another;

a second flexible connecting member;
and a third flexible connecting member, wherein the second flexible connecting member extends between the first substantially rigid element and the third substantially rigid element and permits the first substantially rigid element and the third substantially rigid element to flex relative to one another, wherein the third flexible connecting member extends between the second substantially rigid element and the fourth substantially rigid element and permits the second substantially rigid element and the fourth substantially rigid element to flex relative to one another, wherein the first connecting member also extends between the third substantially rigid element and the fourth substantially rigid element and permits the third substantially rigid element and the fourth substantially rigid element to flex relative to one another, wherein the first and third substantially rigid elements are structured to be suitable for placing over and covering a nasal region of a user, and wherein the second and fourth substantially rigid elements are structured to be suitable for placing over and covering an oral region of a user when the respiratory interface device is used by the user.

2. The respiratory interface device of claim 1, wherein the first connecting member is structured to flex in a hinge-like manner.

3. The respiratory interface device of claim 2, wherein the first connecting member includes a hinge mechanism.

4. The respiratory interface device of claim 3, wherein the hinge mechanism comprises a living hinge.

5. The respiratory interface device of claim 1, wherein the first connecting member has a concave shape relative to a front of the respiratory interface device or a convex shape relative to a front of the respiratory interface device.

6. The respiratory interface device of claim 1, wherein the first connecting member has a variable wall thickness.

7. The respiratory interface device of claim 6, wherein the wall thickness is between 0.5 and 3 mm.

8. The respiratory interface device of claim 1, wherein the first connecting member is constructed of a material having an elongation of between 600% and 800%.

9. The respiratory interface device of claim 1, wherein the first connecting member includes a pleat.

10. The respiratory interface device of claim 1, wherein the first connecting member is constructed of a material selected from the group consisting of thermoplatics, thermoelastomers, and combinations thereof.

11. The respiratory interface device of claim 1, further comprising a support member at least partially connected to the first and third substantially rigid for engaging a portion of a face of the user.

12. The respiratory interface device of claim 1, wherein at least one of the first substantially rigid element and the third substantially rigid elements has a first opening and at least one of the second substantially rigid element and the fourth substantially rigid elements has a second opening.

13. The respiratory interface device of claim 12, wherein the first opening comprises an exhaust port and wherein the second opening is coupled to a coupling device.

14. The respiratory interface device of claim 13, wherein the first opening is removably coupled to an exhaust valve and wherein the second opening is removably coupled to a coupling device.

15. The respiratory interface device of claim 13, wherein the first opening is removably coupled to a cap and wherein the second opening is removably coupled to a coupling device.

16. The respiratory interface device of claim 1, wherein at least one of the second substantially rigid second element and the fourth substantially rigid element are removably coupled to the respiratory interface.

17. The respiratory interface device of claim 1, wherein at least one of the first, second, third, and fourth substantially rigid elements is structured to enable disconnection from the connecting member.

* * * * *